(12) United States Patent
Sokolov

(10) Patent No.: US 9,700,498 B2
(45) Date of Patent: Jul. 11, 2017

(54) METHODS FOR POLISHING A TOOTH SURFACE UTILIZING ABRASIVE NANOPARTICLES

(71) Applicant: Igor Sokolov, Medford, MA (US)

(72) Inventor: Igor Sokolov, Medford, MA (US)

(73) Assignee: Clarkson University, Polsdam, NY (US)

( * ) Notice: Subject to any disclaimer, the term of this patent is extended or adjusted under 35 U.S.C. 154(b) by 0 days.

(21) Appl. No.: 15/006,379

(22) Filed: Jan. 26, 2016

(65) Prior Publication Data

US 2016/0220459 A1 Aug. 4, 2016

Related U.S. Application Data

(63) Continuation of application No. 12/151,558, filed on May 7, 2008, now abandoned.

(60) Provisional application No. 60/924,345, filed on May 10, 2007.

(51) Int. Cl.
| | |
|---|---|
| *A61K 8/25* | (2006.01) |
| *A61Q 11/00* | (2006.01) |
| *A61K 8/29* | (2006.01) |
| *A61K 8/02* | (2006.01) |
| *A61K 8/19* | (2006.01) |

(52) U.S. Cl.
CPC .............. *A61K 8/25* (2013.01); *A61K 8/0241* (2013.01); *A61K 8/19* (2013.01); *A61K 8/29* (2013.01); *A61Q 11/00* (2013.01); *A61K 2800/28* (2013.01); *A61K 2800/413* (2013.01)

(58) Field of Classification Search
None
See application file for complete search history.

(56) References Cited

U.S. PATENT DOCUMENTS

| | | | |
|---|---|---|---|
| 4,144,321 A | | 3/1979 | Wason |
| 4,839,158 A | * | 6/1989 | Michaels ................. A61K 8/40 424/49 |
| 5,369,916 A | * | 12/1994 | Jefferies ............... A61C 15/041 451/490 |
| 5,500,223 A | | 3/1996 | Behan |
| 6,280,707 B1 | | 8/2001 | Peterson |
| 2002/0144705 A1 | | 10/2002 | Brattesani |

(Continued)

OTHER PUBLICATIONS

G Johannsen, G Tellefsen, A Johannsen, A Liljeborg. "The importance of measuring toothpaste abrasivity in both a quantitative and qualitative way." Acta Odontologica Scandinavica, vol. 71, 2013, pp. 508-517.*

(Continued)

*Primary Examiner* — Isaac Shomer
(74) *Attorney, Agent, or Firm* — Blaine T. Bettlinger; George R. McGuire; Bond Schoeneck & King, PLLC

(57) ABSTRACT

A method for polishing tooth surface which eases removal of a bacterial film later grown on the polished surface. The method includes the steps of providing a providing a toothpaste or slurry comprising a plurality of inorganic abrasive particles smaller than 100 nm in size, the inorganic abrasive particles comprising one or more of silica, ceria, titania, zirconia, silicon nitrite, and silica carbide, wherein the inorganic abrasive particles are sufficiently hard to be abrasive; and polishing a tooth surface with the toothpaste or slurry to attain an ultra-smooth tooth surface which can be easily cleaned.

17 Claims, 9 Drawing Sheets

(56) References Cited

U.S. PATENT DOCUMENTS

| | | |
|---|---|---|
| 2003/0111417 A1* | 6/2003 | Paszkowski .......... B01D 61/16 210/653 |
| 2003/0152629 A1 | 8/2003 | Shefer |
| 2003/0181541 A1* | 9/2003 | Wu ..................... A61K 6/0017 523/115 |
| 2004/0161388 A1 | 8/2004 | Liu |
| 2005/0027040 A1 | 2/2005 | Nelson |
| 2005/0220829 A1* | 10/2005 | Sung ....................... A61K 8/11 424/401 |

OTHER PUBLICATIONS

H Yurdaguven, A Aykor, E Ozel, H Sabuncu, M Soyman. "Influence of a prophylaxis paste on surface roughness of different composites, porcelain, enamel and dentin surfaces." European Journal of Dentistry, vol. 6, Jan. 2012, pp. 1-8.*

Kim, G., Kim, H., Park, B., Lee, H., Park, K., Effect of Abrasives Concentration and Size in ILD Chemical Mechanical Polishing, 2004, pp. 119-128.

Aerisil 200 Product Information. Fluffy Aerosil Powder.

* cited by examiner

METHODS FOR POLISHING A TOOTH SURFACE UTILIZING ABRASIVE NANOPARTICLES

CROSS REFERENCE TO A RELATED APPLICATION

This application is a continuation of U.S. patent application Ser. No. 12/151,558, filed on May 7, 2008 and entitled "Nanoparticles as an Abrasive to Polish Tooth Surface," which claims priority to U.S. Provisional Application Ser. No. 60/924,345 filed on May 10, 2007 entitled "Silica Nanoparticles As An Abrasive To Polish Tooth Surface," the entirety of which are both hereby incorporated by reference.

FIELD OF THE INVENTION

The invention relates to the use of nanoparticles as an abrasive component of dental prophylactic compounds including toothpastes or polishing dental slurries.

BACKGROUND

Tooth polishing in dentistry is well known. Many companies have come forward with their techniques to polish tooth surfaces. Polishing of tooth surfaces is used to make these surfaces smooth making it difficult for plaque, consequently, tartar and debris that causes cavities to accumulate on teeth. Hence polishing is a preventive procedure used as an initial defense against dental problems.

The following patent applications and patents discuss or at least partially about abrasives in toothpaste:

U.S. Pat. No. 5,866,630: by Mitra et al. entitled "Optionally Crosslinkable Coatings Compositions and Methods of Use" discusses coatings for hard tissue and surfaces of the oral environment are provided that reduces adhesion of bacteria and proteinaceous substances to these surfaces. Methods of reducing adhesion of these materials to such surfaces, and polymers for incorporation into such coatings are provided.

U.S. Pat. No. 7,303,600 by Roulston et al. entitled "Unexpanded Perlite Ore Polishing Composition and Methods" discusses an unexpanded perlite ore polishing composition. The composition comprises base material having grains of unexpanded perlite ore of a selected distribution of particle sizes which undergo fracturing of the grains as a function of an abrasive force applied to the base material. The selected distribution of particle sizes includes a significant volume of grains of unexpanded perlite ore having a (d90) particle size in a range of about 101 to about 229 gm. The base material is responsive force being applied thereto during polishing resulting in fracturing of the grains unexpanded perlite ore to yield a final composition having a sufficiently low level of abrasiveness under said abrasive force making it suitable for use in polishing. Compositions for polishing acrylic dentures and CRT tube surfaces using the unexpanded perlite ore composition and methods for polishing the same are also shown.

US Patent Application 2006/0140879 entitled "Two Phase Toothpaste Composition" by Fruge et al. discusses an oral care composition having a first phase of clinically efficacious 2,4,4'trichloro 2'-hydroxydiphenyl ether admixed in a first orally acceptable aqueous vehicle, and a second phase having a stannous salt (such as stannous fluoride) admixed in a second orally acceptable aqueous vehicle. The second phase has no less than 10 molar percent of soluble stannous ion respective to a mathematical sum of moles of the soluble stannous ion and moles of the stannous salt in the second phase. In one embodiment, the two phases are provided in a dual-tube toothpaste oral care kit.

US Patent Application Number 2005/0210615 entitled "Oral Care Method" by Shastry et al. discloses a method for improving effectiveness of an oral care agent that comprises preconditioning an oral surface by wiping the surface with an absorbent fabric having impregnated therein or coated thereon an orally acceptable preconditioning agent such as an activating agent for the oral care agent, wherein the wiping transfers an activating effective amount of the preconditioning agent from the fabric to the oral surface, and thereafter applying a composition comprising the oral care agent to the oral surface.

US Patent Application Number 2005/008446 entitled "Tooth Enamel Rejuvenating Toothpaste" by Winston et al. discloses an oral composition provided which is effective for mineralization of surface enamel comprising a first part containing a partially water soluble calcium salt and a second part containing a fluoride salt and a bicarbonate salt. The oral composition can be a toothpaste and wherein the second part preferably contains sufficient bicarbonate salt to provide a fresh, clean feeling to the oral cavity.

U.S. Pat. No. 6,280,707 entitled "Oral Prophylaxis Paste" by Peterson et al. discloses an oral prophylaxis paste that includes a preselected grade and amount of abrasive material as pumice clay or diatimoceous earth. The abrasive material is moistened with water and a moisture retention agent such as glycerin is included. A curing system is employed such as using sodium silicate and methyl salicylate. The formulation provides antimicrobial properties by the inclusion of triclosan.

U.S. Pat. No. 5,1087,734 entitled "Prophy Mouthfeel Dentifrice Having Low RDA Value" by Colodney et al, discloses a dentifrice cream composition and the process for its preparation. The dentifrice has an RDA value less than 150 which provides a crunchy prophyl mouthfeel to the user during tooth brushing. The dentifrice comprises a vehicle having dispersed therein a siliceous polishing agent having a particle size distribution of about 1 to about 100 microns wherein (1) more than 25% of the particles have a size greater than about 40 microns and (2) at least about 10% of the particles of (1) have a particle size greater than about 60 microns and at least about 5% of the particles have a particle size greater than about 80 microns. In the preparation of the dentifrice, the dispersion of the silica particles in the dentifrice is accomplished under low shear conditions.

SUMMARY

Tooth polishing is a common practice in modern dentistry. Abrasives used in this process are large sized particles (0.1 micron to hundreds of microns). Here we disclose the use of nanoparticles as abrasives for tooth polishing. Considerably lower (compared to regular polishing paste) nanometer levels of roughness of the tooth surface can be obtained when using the nanoparticles. This helps to protect tooth surface against the damage caused by cariogenic bacteria because the bacteria could be easily removed from such a polished tooth surface.

This invention illustrates the use of abrasive nanoparticles as an additive component of tooth pastes. The abrasive additives include hard inorganic oxide particles that are smaller than 100 nm in size, either particles of one nature or a mix of particles of different natures. Additionally the abrasive additives include particles composed of silica, ceria, titania, zirconia, silicon nitrite, silica carbide, and others that are sufficiently hard to produce abrasive action, and are benign for humans. To demonstrate the essence of the invention, colloidal silica particles of average size of 60 nm are utilized. The process may use commercial slurries containing nanoparticles, in which the chemistry of the slurry is adjusted to be usable/harmless for humans. These slurries may include commercial slurries containing silica or ceria nanoparticles. The process includes the use of polyurethane polishing pads to polish human teeth. The process also illustrates the use of atomic force microscopy to detect removal of bacteria from dental surfaces.

The invention is having nanoparticles as one or more of the abrasive additive components of the inventive tooth paste or polishing slurry. These abrasive additives comprise hard inorganic oxide particles of one nature or a mix of particles of different natures that are smaller than 100 nm in size. The inventive tooth paste has abrasive additives that are particles selected from the group consisting of silica, ceria, titania, zirconia, silicon nitride, silica carbide, and others that are sufficiently hard to produce abrasive action, and being benign for humans. The colloidal silica particles are of an average size of 60 nm. The inventive tooth paste includes slurries containing the nanoparticles with the chemical formulation of the slurry is adjusted to be usable for humans. The slurries used contain silica nanoparticles. The inventive tooth paste/slurry has a RDA value in excess of 750. It may as well have an RDA value in excess of 1000. The inventive tooth paste/slurry with nanoparticles creates a tooth smoothness of less than 5 nm. As an example, polyurethane polishing pads are used to polish human teeth using said inventive tooth paste/slurry.

The inventive method of detecting the removal of bacteria from dental surfaces uses atomic force microscopy (AFM). The AFM method uses an atomic force microscope in the scan mode and/or the raster mode. Specifically, atomic force microscopy is used to provide a measurement of the effectiveness of the removal of bacteria from dental surfaces and to provide a measurement of the abrasiveness of various tooth pastes.

These and other features, aspects, and advantages of the present invention will become better understood with regard to the following description, appended claims, and accompanying drawings.

DETAILED DESCRIPTION

The use of nanoparticles to polish tooth surfaces show the advantage of attaining faster polishing and smoother surface of teeth. It is a known observation in the modem semiconductor industry; as discussed by Lu, Z., N. P. Ryde, et al. (2005) in "Particle adhesion studies relevant to chemical mechanical polishing" Langmuir 21(22): 9866-72 hereby incorporated by reference; that in general the surfaces polished with nanosize abrasive particles get noticeably smoother. However, as known in the same chemical mechanical polishing (CMP) methods, it is not guaranteed that one gets smoother surface just taking finer abrasive particles. CMP companies have spent millions of dollars to insure that property. Here we disclose the use of polishing slurry that leads to nanometer-scale roughness of polished tooth surfaces.

Furthermore, we disclose that bacteria adhered to smoother surfaces can be more easily removed than from rough surfaces, thereby preventing them from formation of plaques and ultimately keeping bacteria away from tooth surfaces. This is not an obvious result because bacteria attaches to the tooth surface via biochemical means, and therefore can simply ignore the said difference in roughness before and after the polishing. In general, the forces of interaction of an organic substance with flat surfaces are comparatively weaker than with rough corrugated surfaces because of the increased area of the rough surface compared to the flat one. In the case of bacterial attachment, it may not necessarily be that simple. For example, bacteria could still strongly attach even to a rather smooth surface, so the difference in the adhesion could be negligible when we consider the nanoscale roughness. We show that the addition of nanoparticles makes a toothpaste or a polishing slurry that utilizes such abrasives helpful to remove the bacteria, and consequentially, protect teeth against damaging by cariogenic bacteria.

While particles can be of any biocompatible nature (ceria, gold, silica, diamond, alumina, titania, and so on), various shapes, and the sizes from 0.001 to 0.1 microns, as an example, we demonstrate the use an abrasive with 60 nm spherical silica particles.

Materials and Methods:
Characterization

Figure 1:
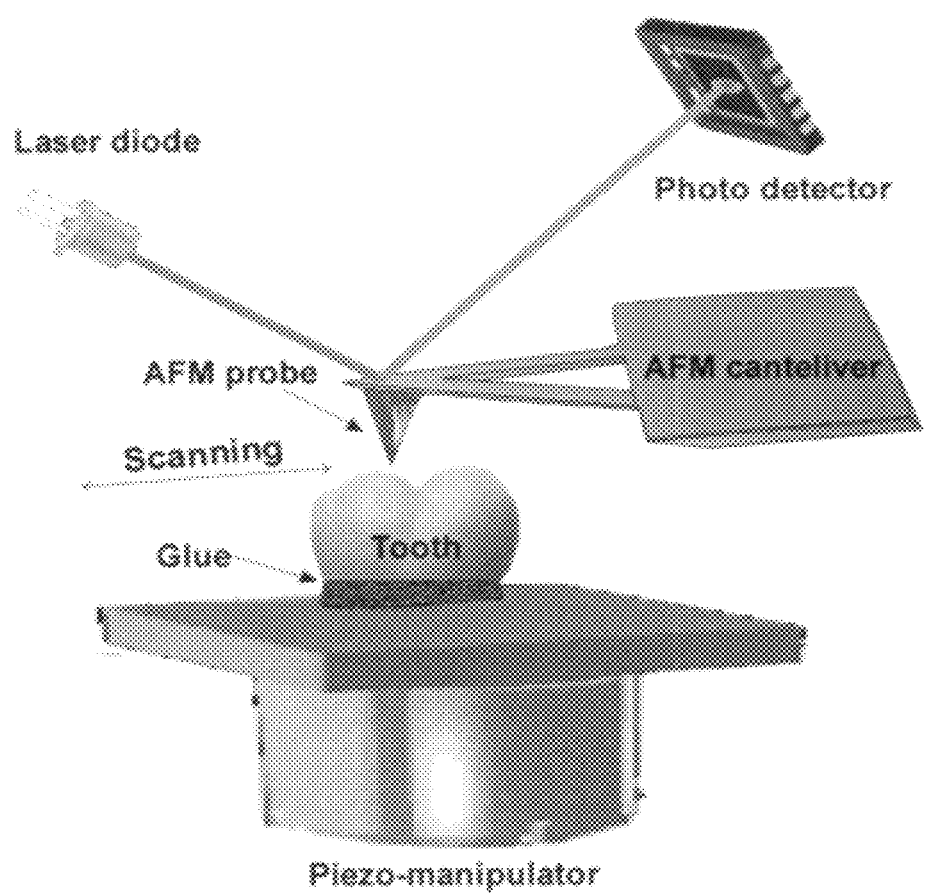
FIG. 1 illustrates a schematic of an Atomic Force Microscope setup, in accordance with an embodiment.

The Atomic Force Microscope (AFM) is a relatively novel method of measurement as discussed by Binnig, G., C. F. Quate, et al. (1986) in "Atomic force microscope." *Phys. Rev. Lett.* 56(9): 930-933, hereby incorporated by reference. This technique is based on the detection of forces acting between a sharp tip, the AFM probe, and sample surface, for example, tooth surface. FIG. 1 illustrates the schematics of the AFM setup. The AFM probe is attached to a flexible cantilever. A laser beam is reflected from the cantilever and detected by a photodiode. Thus, any vertical displacements of the cantilever are detected by the photodiode. When scanning, the probe is brought to a contact, engaged with the surface of interest. Scanning over the surface, the AFM system records the deflection of the cantilever with sub-nanometer precision. The deflection signal (or any derivatives of the deflection) is recorded digitally, and can be visualized on a computer in real-time.

The AFM technique is much more than just simply the microscopy described above. One can think about the AFM probe as a microscopic "finger" with a nanosize apex. Here we use the AFM probe as a sort of a soft brush to remove bacteria from the tooth surface while imaging the tooth surface in contact mode. This method will be described in more detail below.

Here we use a Nanoscope™ Dimension 3100 AFM (Veeco/DI Instruments, Inc., Santa Barbara, Calif.). A standard cantilever holder cell for operation in liquids is employed. Roughness measurements are done with the built-in AFM software (version used 5.12, release 4). All scanning measurements are performed on the tooth surface immersed in deionized water. A V-shaped standard wide 200 p.m AFM cantilevers (Veeco, Santa Barbara, Calif.) were used throughout our study. The contact mode is used for AFM imaging. The scan speed of 2-4 Hz is used while imaging in contact mode, 15 Hz is used for the raster mode used to monitor removal of the bacteria. When using the rastering mode, the scan angle is set to 90 degrees to provide homogeneous lateral force (friction force) responsible for the bacteria removal.

Bacterial Culture

*Streptococcus Mutans* (Wards-Lyophilized Bacteria 85-1957) are received as freeze-dried. It is regenerated by dissolving in 5 ml of culture medium (tryptic soy broth) for a minute, and then, placing tooth sample in the growth medium overnight. About 5 ml of the bacterial solution (bacteria and culture medium) is centrifuged for about 5 min at 3000 rev/min and the supernatant is discarded carefully to retain the pellet of bacteria at the bottom of the test tube. The pellet is then resuspended in 3 ml of deionized water to wash away the culture medium and acid produced by the bacteria. In culture medium, the optimum pH for growth of a bacterium must be considered and hence sodium acetate buffer is used to maintain the pH of the medium depending on bacterial waste products (acids) that accumulate during growth. Most bacteria exhibit a relatively narrow range of pH over which they grow. Also they grow over a temperature range of about 37 degrees. The bacteria is again centrifuged and the pellet is resuspended in a solution of 15% glucose and sodium acetate pH 5.0 (the buffer to maintain the pH of the culture medium). This bacterial solution is applied on tooth surface to form films.

To grow the bacterial films on the tooth surface, the tooth samples are then immersed in bacterial suspension overnight in water bath (American Optical Model #406015) at 37° C. The sample is rinsed with DI water from the sides to remove excess of bacterial colonies from the sample.

Tooth Samples

The tooth samples used for the research are milk teeth. The surfaces are not treated with any chemicals for our study. The milk tooth is cut into four pieces using a cutter and each piece is fixed to a glass slide with water insoluble glue (Loctite E-30CL Hysol epoxy adhesive) with their enamel facing up. The glue is allowed to cure overnight.

Polishing Slurry, Tooth Preparation for Polishing, and Bacteria Treatment

The abrasive slurry used here is prepared from 60 nm colloidal silica particles in aqueous medium of neutral pH (is adjusted with acetic acid (Fisher Scientific)). The particles are used from a commercial slurry (Klebosol, Rodel ILD 1300). The polishing is done with a polyurethane polishing pad (Rodel IC 1400) attached to a polishing machine (Lecco Corporation GP-10, Grinder and Polisher). A load of 5 g is attached to the end of glass slide where the tooth is glued. The sample to be polished is held gently on the rotating polishing pad. There is a constant flow of slurry. After about 20 sec the tooth is viewed under an optical microscope to check for the amount of polish. In order to image the tooth surface under AFM the tooth is removed from the glass surface and glued to a Petri dish (35×10 mm). The tooth sample is ready to be immersed in bacterial suspension.

The tooth samples are immersed in bacterial suspension overnight in water bath (American Optical Model #406015) at 37° C. The sample is rinsed with DI water from the sides to remove excess of bacterial colonies from the sample.

The polishing paste used for the study is the commercially available Crest® cavity protection regular paste (Proctor &Gamble, Inc.) and a specialized paste NUPRO® with fluoride (Orange—fine grit as well as Mint—medium grit (Dentsply Caulk, Inc.) used by dentists for cleaning of tooth surface. The abrasives used in Crest® tooth paste are of the order of micrometers whereas those in the NUPRO® paste range from 1-177 µm depending on whether it is fine or coarse grit.

The tooth paste Crest® as well as NUPRO® (5 g) are dissolved in 10 ml of DI water and stirred for 5 min. The tooth samples are polished as mentioned above, but the slurry is replaced with the solution of the Crest® and NUPRO® pastes, respectively. The sample is observed under microscope for desired polish surface and is engaged for 2 min.

Staining of Bacteria for Optical Visualization

Aqueous solution of methylene blue dye (biological grade, Sigma-Aldrich, Inc.) is used to visualize bacteria adhered to the tooth surface. Bacterial film as formed on tooth surface is stained with a few drops of methylene blue for about 2 min and then rinsed with water to wash away excess dye from tooth surfaces. Such a staining allows optical differentiating between bacteria and dental surface, which stays white while bacteria become bluish.

Polishing Procedure

Figure 2:
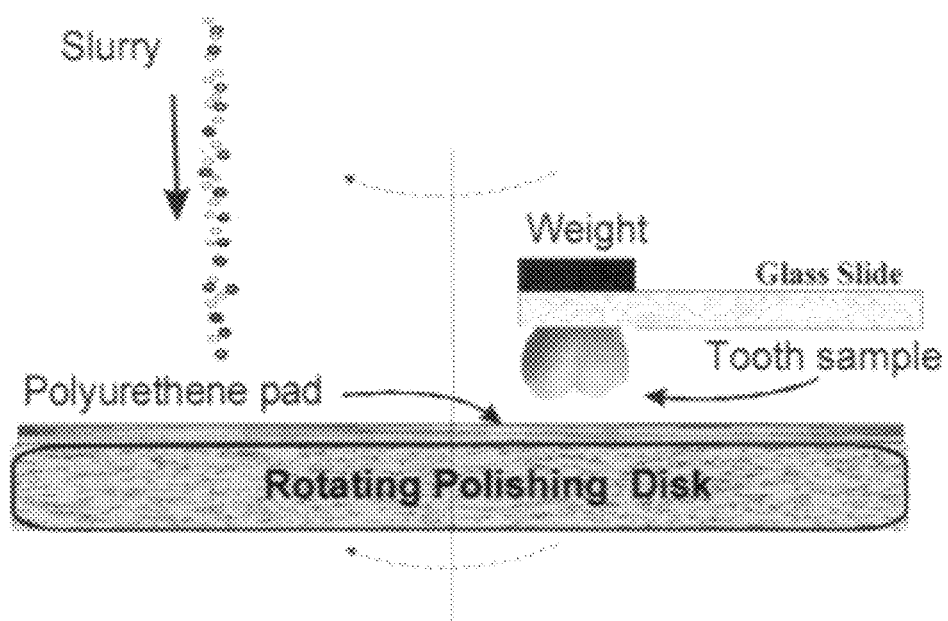
FIG. 2 illustrates a schematic of polishing, in accordance with an embodiment.
Figure 3A:
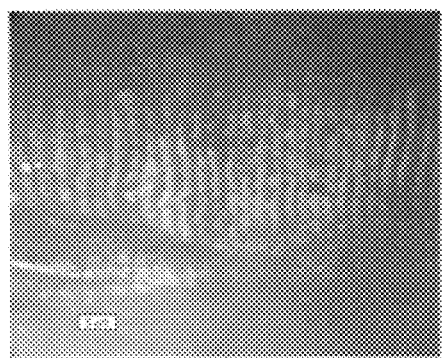
FIG. 3A illustrates an optical image of a virgin tooth.
Figure 3B:
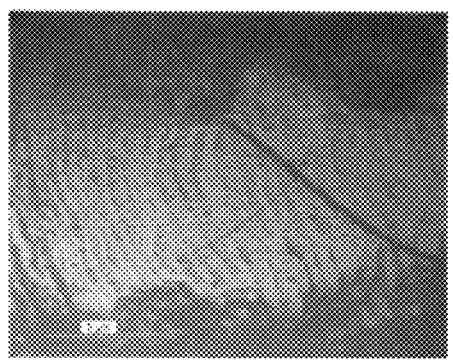
FIG. 3B illustrates an optical image of a toothpaste (Crest®) polished tooth, in accordance with an embodiment.
Figure 3C:
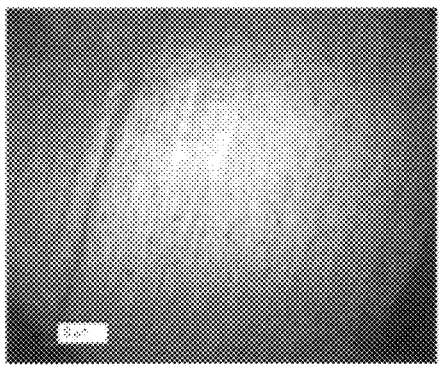
FIG. 3C illustrates an optical image of a dental toothpaste (NUPRO®) polished tooth, in accordance with an embodiment.
Figure 3D:
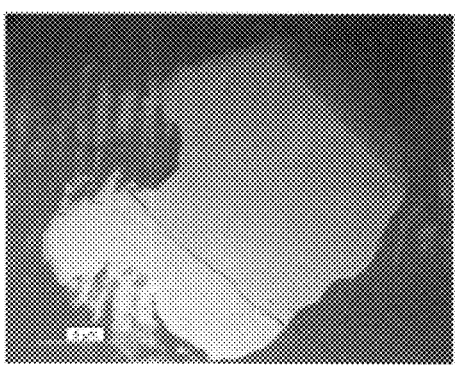
FIG. 3D illustrates an optical image of a slurry polished tooth, in accordance with an embodiment.
Figure 4A:
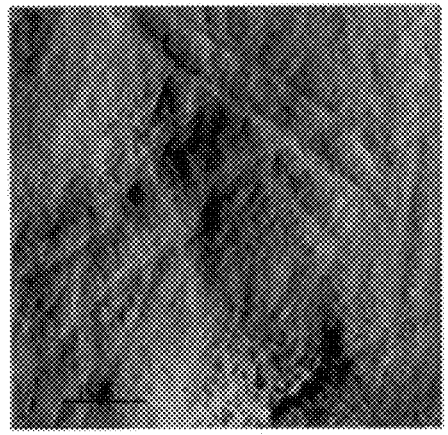
FIG. 4A illustrates a 15×15 $\mu m^2$ Atomic Force Microscope image of a virgin tooth, in accordance with an embodiment.
Figure 4B:
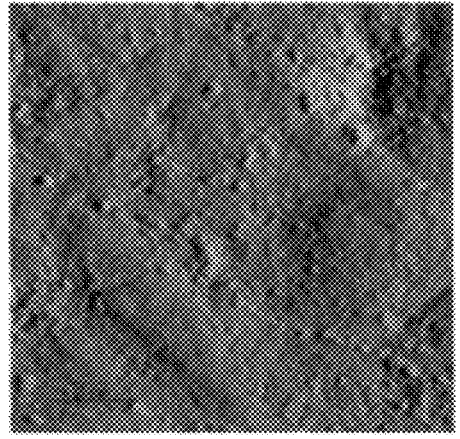
FIG. 4B illustrates a 15×15 $\mu m^2$ Atomic Force Microscope image of a toothpaste (Crest®) polished tooth, in accordance with an embodiment.
Figure 4C:
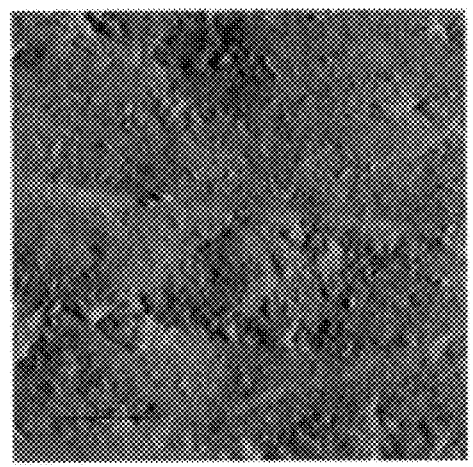
FIG. 4C illustrates a 15×15 $\mu m^2$ Atomic Force Microscope image of a dental toothpaste (NUPRO®) polished tooth in accordance with an embodiment.
Figure 4D:
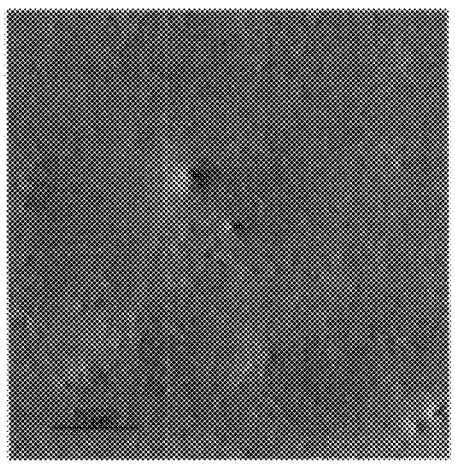
FIG. 4D illustrates a 15×15 $\mu m^2$ Atomic Force Microscope image of a slurry polished tooth, in accordance with an embodiment.
Figure 5A:
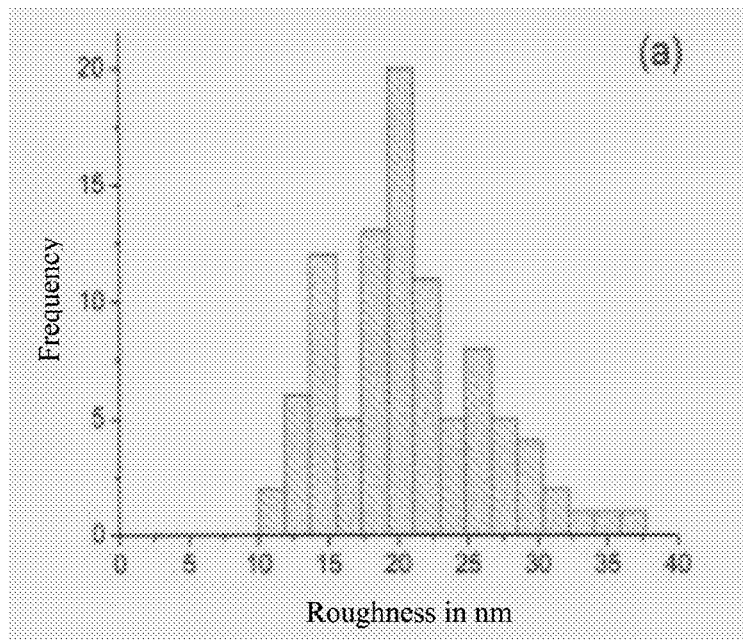
FIG. 5A illustrates a roughness distribution for a virgin tooth surface, in accordance with an embodiment.
Figure 5B:
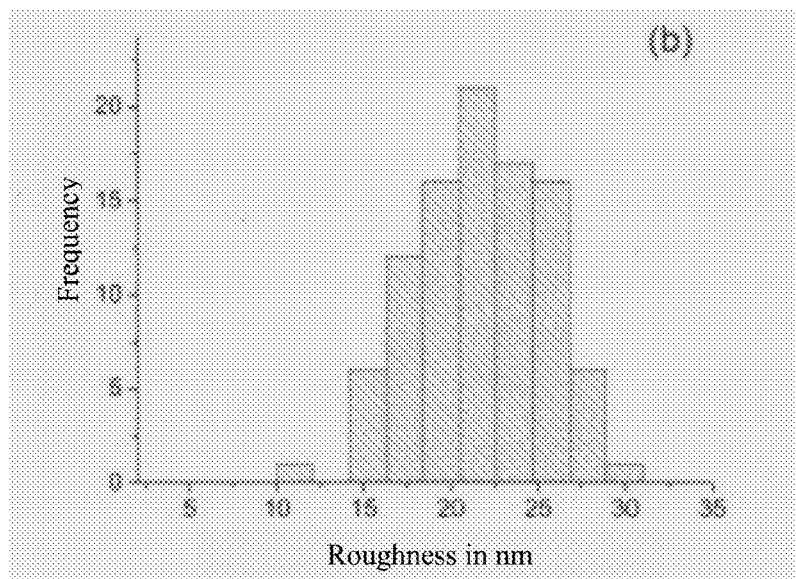
FIG. 5B illustrates a roughness distribution for a tooth paste (Crest®) polished tooth surface, in accordance with an embodiment.
Figure 5C:
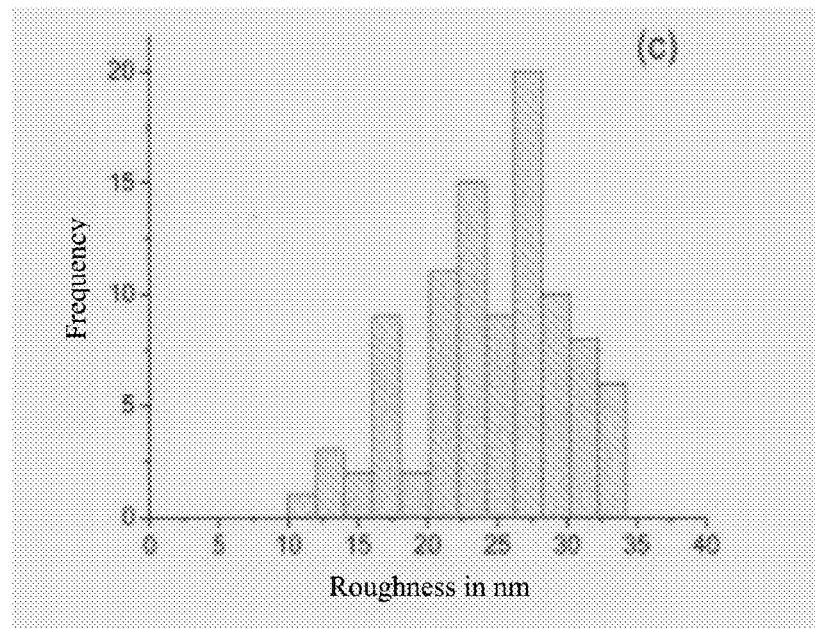
FIG. 5C illustrates a roughness distribution for a NUPRO dental toothpaste (NUPRO®) polished tooth surface, in accordance with an embodiment.
Figure 5D:
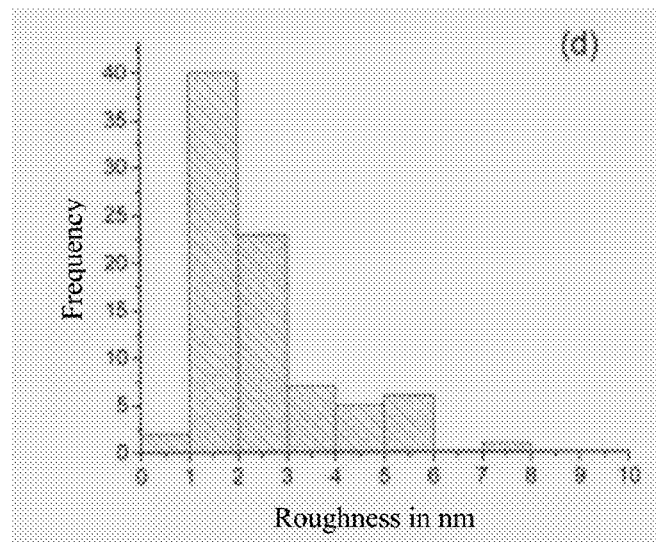
FIG. 5D illustrates a roughness distribution for a slurry polished tooth surface, in accordance with an embodiment.

The polishing is done by using a polyurethane pad (IC1400, Rodel, Inc.) attached to a polishing machine (Lecco Corporation GP-10, Grinder and Polisher). A load of 5 gm is attached to the top of one end of glass slide where the tooth is glued, see FIG. 2. The other side of glass slide is gently held by fingers. A constant flow of slurry of nanoparticles is supplied. After about 20 sec of polishing, the tooth is checked under an optical microscope to estimate the degree of polishing. Similar procedure but with longer polishing times of about 1 to 2 min is used when using commercially available Crest® cavity protection regular paste (Procter and Gamble, Inc.), and a specialized polishing paste NUPRO® with fluoride (fine grit, Dentsply Caulk) used by dentist for cleaning of tooth enamel. The longer times in the latter case are used to attain approximately the same removal of the enamel during the polishing (as is qualitatively estimated by optical microscopy). In order to image the tooth surface under AFM the tooth sample is placed in a Petri dish.

Results

Roughness Measurement.

We compare roughness of virgin tooth surface and the surface of the same tooth (split into four pieces) when polished with, tooth paste, polishing paste, and nanoparticle slurry. Optical images of these four surfaces are illustrated in FIG. 3.

FIGS. 4A-D shows representative AFM images of the surfaces shown in FIGS. 3A-D. As one can see from these images, the slurry polished tooth exhibited a smoother surface than the tooth paste polished surface. One can see that the surfaces polished with Crest® and NUPRO® look even rougher at micron scale than the virgin tooth. This is not very surprising as both toothpastes are not intended to provide the polishing at nanoscale. FIG. 3 illustrates Optical Images of (FIG. 3A) virgin tooth, (FIG. 3B) a toothpaste polished tooth, and (FIG. 3C) a dental toothpaste (NUPRO®) polished tooth and (FIG. 3D) Slurry polished tooth. FIGS. 4A-D illustrates a series 15×15 μm² AFM images of (FIG. 4A) virgin tooth, (FIG. 4B) a toothpaste (Crest®) polished tooth, and (FIG. 4C) a dental toothpaste (NUPRO®) polished tooth, and (FIG. 4D) a slurry polished tooth.

Roughness Analysis:

Quantitative analysis of roughness is done for the areas of 5×5 μm². This is justified by the size of S. mutans bacteria. We assume that the roughness should be analyzed over the area comparable with the bacterium size to contribute to the bacterial adhesion. This is plausible because it is unlikely that a bacterium would develop adhesion to an area much larger than its size. Statistical distributions for the roughness obtained are as illustrated in FIGS. 5A-5D. Each roughness measurement corresponds to a region of 5×5 μm² extracted from a larger 20×20 μm² image. In total, 8 images of 20×20 μm² are recorded, and each image divided into approximately 10-16 images of 5×5 μm².

FIGS. 5A-5D illustrate a roughness distribution for (5A) a virgin tooth, (5B) a tooth paste polished tooth, (5C) a NUPRO® polished tooth, and (5D) a slurry polished tooth surface. The average roughness and standard deviation (with respect to the normal distribution) of the distributions of FIGS. 5A-D are shown in Table 1. One can see that on sub 5-micron level neither Crest® nor NUPRO® pastes improved the roughness. This is in agreement with both optical images of FIGS. 3A-D and AFM images of FIGS. 4 A-D. The surface polished with the slurry of nanoparticles show an order of magnitude decrease in roughness. In the next section we will discuss if this decrease is significant by the bacterial adhesion. Table 1 illustrates average roughness and standard deviation of the tooth surfaces both virgin and polished.

TABLE 1

| Tooth sample | Average Roughness (nm) | Standard Deviation (nm) |
|---|---|---|
| Virgin | 20.7 | 5.5 |
| Crest ® polished | 21.7 | 3.6 |
| NUPRO ® polished | 24.5 | 5.2 |
| Slurry polished | 2.4 | 1.4 |

Bacteria Adhesion to Surfaces of Different Roughness: AFM Study

To correlate the adhesion of S. mutans bacteria to the tooth surface with surface roughness, we used the raster AFM scanning method briefly described in the Materials and Methods section. This technique is analogous to the action of a single fiber of a soft cleaning brush. The AFM probe scans/rasters rather fast over the tooth surface. See FIG. 6. Because we are working in the contact mode, the rastering is done with a constant load force. This helps to monitor removal of the bacteria in a highly controlled way.

Figure 6:
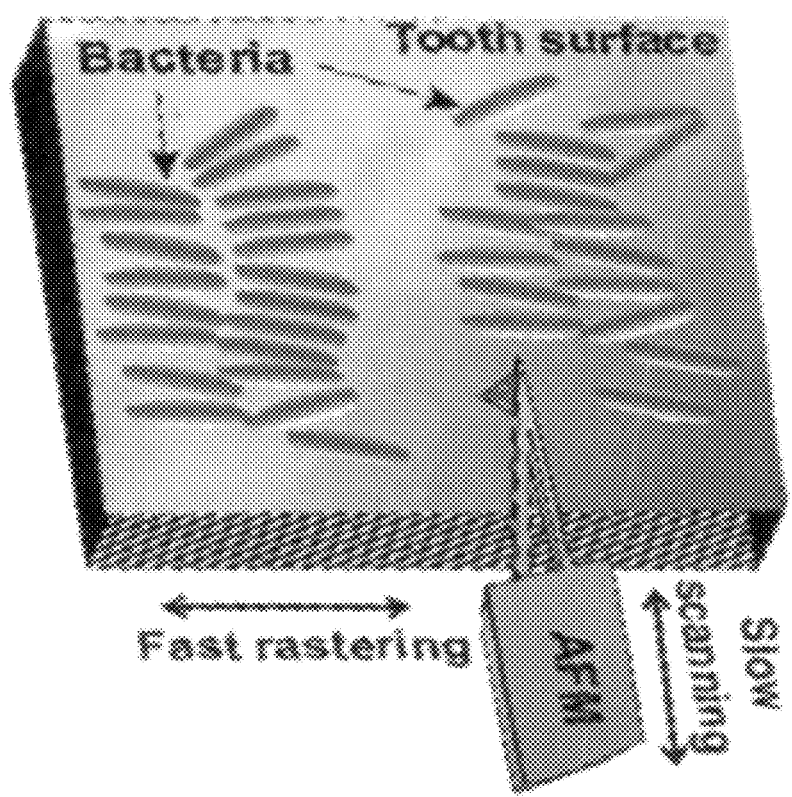
FIG. 6 illustrates a schematic of a rastering mode of an Atomic Force Microscope, in accordance with an embodiment.

FIG. 6 illustrates a schematic of rastering mode. During the rastering, the AFM probe moves left-right fast, while slowly scanning up and down. The bacteria attached to the surface can be removed by the, action of lateral force of the AFM probe. This mimics the action of a single fiber of a soft cleaning brush.

Figure 7A:
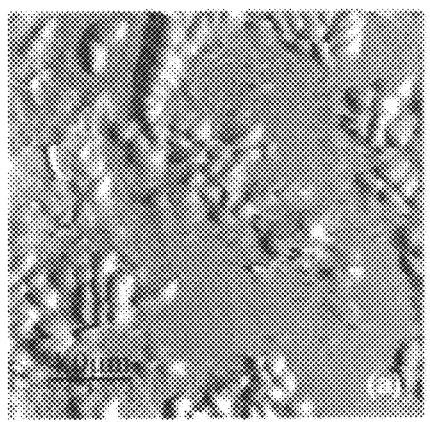
FIG. 7A illustrates an Atomic Force Microscope image of a slurry polished tooth surface with S. mutans adhered, in accordance with an embodiment.
Figure 7C:
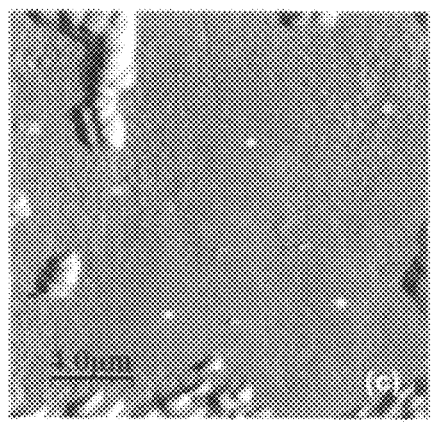
FIG. 7C illustrates an Atomic Force Microscope image of a slurry polished tooth surface with S. mutans adhered, in accordance with an embodiment.
Figure 7B:
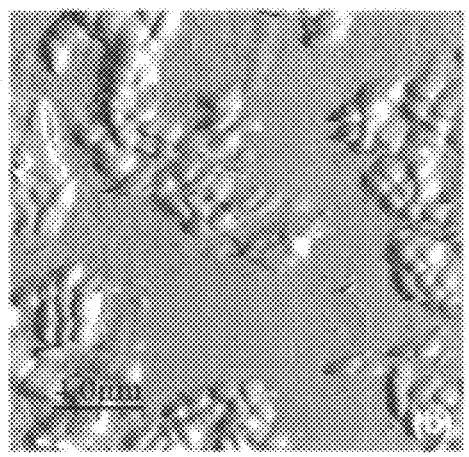
FIG. 7B illustrates an Atomic Force Microscope image of a slurry polished tooth surface with S. mutans adhered, in accordance with an embodiment.

After the first scans, weakly attached bacteria are removed by the action of lateral force of the AFM probe. After several scans, more tightly attached bacteria are also removed. And finally, the bacteria with strongest adhesion are removed last. While rastering, AFM can, in principle, collect the images of the surface with the bacteria on it, although quality is insufficiently low. We used those images only to monitor when we need to stop and make a regular, slow AFM scan. FIGS. 7A-C illustrate a series of such images of slurry polished tooth surface with S. mutans adhered, which are taken after certain number of scans. The total scanning period is about 2 minutes, completing approximately a dozen full scans. FIG. 7A is taken after initial couple of scans. It shows exposed relatively small areas of tooth surface, which initially is covered with a continuous layer of bacteria. FIG. 7B shows the bacterial adhesion after approximately 1 minute. FIG. 7C demonstrates the remaining bacteria as at the end of the scan series. One can see that the bacteria are initially removed from the smooth area, FIG. 7A and stayed longer on the rougher one, FIGS. 7B and 7C. Quality of the images is enough to find roughness of those corresponding areas. It is estimated that the roughness of the areas in which the bacteria are removed after the first scans (shown in FIG. 7C with stars) ranges within 1.8-2.4 nm. In contrast, the areas in which bacteria are removed only after the complete series of scans (shown in FIG. 7C with squares) have the roughness of 5.0-5.5 nm. Thus, we can conclude that the adhesion of S. mutans to the polished tooth surface is well correlated with the roughness at nanoscale.

FIGS. 7 A-C illustrate a series of AFM images of a slurry polished tooth surface with S. mutans adhered. One can clearly see that bacteria are easier removed from the smooth surfaces than those adhered to the rougher surfaces.

Bacteria Adhesion to Surfaces of Different Roughness: Optical Visualization

The AFM is a highly precise technique. However, to get a better idea about how representative the results obtained in the previous sections are, we complement those results with a rather simple qualitative method. We monitor the removal of the bacterium film with a regular optical microscopy. To show the advantage of highly polished surfaces for bacteria removal, we use a soft painting brush (made of squirrel tail fur). Methylene blue is commonly used in Gram stains. Here we found that this dye allows us clean differentiation between *S. mutans* and tooth enamel.

Figure 8A:
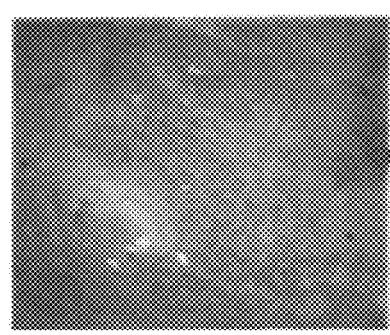
FIG. 8A illustrates an optical image demonstrating removal of bacterial films from the partially polished tooth surface at macroscale (1.5 mm in width), in accordance with an embodiment.

A continuous bacterial film is stained in blue as seen in FIG. 8A. The soft painting brush is gently used to remove this film. This is monitored under bright field reflected optical microscope at certain intervals. The gradual removal of the bacterial film from the surface polished with nanoparticle slurry took a minute, FIGS. 8B and 8C. One can see the polished area as a shiny exposed region. (T junction of two trenches is used as a landmark to find the same area on the optical microscope after cleaning with the brushes.) But in order to get rid of all the bacterial films, a hard brush is used to get a clean surface as seen from the final image, FIG. 8D.

Figure 8B:
FIG. 8B illustrates an optical image demonstrating removal of bacterial films from the partially polished tooth surface at macroscale (1.5 mm in width), in accordance with an embodiment.
Figure 8D:
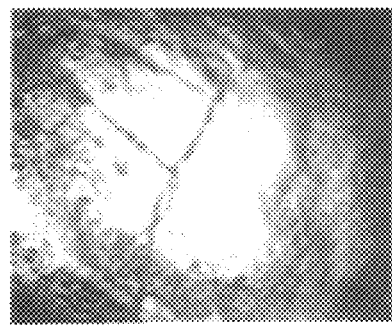
FIG. 8D illustrates an optical image demonstrating removal of bacterial films from the partially polished tooth surface at macroscale (1.5 mm in width), in accordance with an embodiment.
Figure 8C:
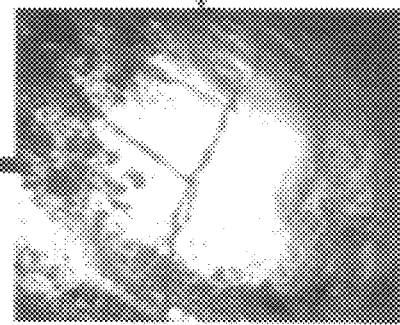
FIG. 8C illustrates an optical image demonstrating removal of bacterial films from the partially polished tooth surface at macroscale (1.5 mm in width), in accordance with an embodiment.

FIGS. 8A-D illustrate optical images demonstrating removal of bacterial films from the partially polished tooth surface at macroscale (each image is 1.5 mm in width). Dark bluish spots are the bacterial films (stained with methylene blue dye). FIG. 8A illustrates a surface completely covered with the film. FIGS. 8B and 8C illustrate surfaces after some gentle cleaning with a soft brush (FIG. 8B preceding FIG. 8C). FIG. 8D illustrates the surface after the hard brush cleaning.

The Dentin Abrasion Values of various dental products is outlined in U.S. Pat. No. 6,280,707 ('707), hereby incorporated by reference, assigned to Dentsply International, Inc. describes the product now known as NUPRO®. RDA (Radioactive Dentin Abrasion) value is measured according to the process described in Hefferen, J. Dent. Res., Vol. 55, No. 4, pp. 563-573, hereby incorporated by reference. The prophylaxis paste according to the present invention has abrasion values above those of the dentifrices currently known commercially. The abrasive ratings provided below gives an example of the commercial prophy pastes and their relative dental abrasion (RDA) values.

Product having Dentin Abrasion (RDA) Values include NUPRO® Paste Fine Grit, 704; NUPRO® Paste Medium Grit, 256; NUPRO® Paste Coarse Grit, 362; Crest® Regular Toothpaste, 81; Crest® Tartar Control Toothpaste, 126; Colgate® Tartar Control Toothpaste, 112; Aim® Tartar Control Toothpaste, 127; Aquafresh® Tartar Control Toothpaste, 125 and Close-up Tartar Control Toothpaste, 120 as shown in the '707 patent. The slurry polish of the instant invention has estimated RDA values in excess of 750 and may exceed 1000.

The RDA value as used in the present description may be determined by any of the standard methods including the Grabensteder method or the Hefferen method. The Hefferen method is preferred because it is recognized by the American Dental Association. While the RDA is the method for evaluation the abrasive nature of normally, toothpaste, another method known as the relative enamel abrasion (REA) is normally used for evaluating prophy paste. There is no specific correlation between the recognized RDA and REA test methods. According to the present invention, a prophy paste having a REA value of preferably above about 5 is within the scope of the invention.

In dentistry there is a concern for the existence of too a high a value of abrasiveness. The method described herein minimizes that because the effects of high abrasiveness can be decreased by adding various chemical elements. A high RDA is more effective because it polishes faster. As discussed above, the main advantage/difference of the inventive slurry/paste is that the inventive slurry makes the dental surface very smooth.

As discussed above AFM is used to measure the roughness of dental surface. The data gathered from such a measurement may be used to develop a measurement of the abrasiveness and effectiveness of various tooth pastes.

Then illustrative embodiments and modifications thereto described hereinabove are merely exemplary. It is to be understood that other modifications to the illustrative embodiments will readily occur to persons of ordinary skill in the art. All such modifications and variations are deemed to be within the scope and spirit of the present invention as will be defined in the accompanying claims.

REFERENCES

Binnig, G., C. F. Quate, et al. (1986). "Atomic force microscope." *Phys. Rev. Lett.* 56(9): 930-933. Lu, Z., N. P. Ryde, et al. (2005). "Particle adhesion studies relevant to chemical mechanical polishing." *Langmuir* 21(22): 9866-72.

What is claimed is:

1. A method for polishing a tooth surface, the method comprising the steps of:
   providing a toothpaste comprising a plurality of inorganic abrasive particles smaller than 100 nm in size, the inorganic abrasive particles comprising one or more of silica, ceria, titania, zirconia, silicon nitrite, and silica carbide, wherein the inorganic abrasive particles are sufficiently hard to be abrasive; and
   polishing a tooth surface with the toothpaste such that a roughness of the tooth surface is reduced, wherein said polishing step results in a tooth surface smoothness of less than 5 nm.

2. The method of claim 1, wherein the tooth surface is polished for approximately 20 seconds to 2 minutes.

3. The method of claim 1, wherein said plurality of inorganic abrasive particles comprise an average size of approximately 60 nm.

4. The method of claim 1, further comprising the step of removing a bacterial film from the polished tooth surface without a toothbrush.

5. The method of claim 4, wherein the removing step comprises rinsing the tooth surface with water.

6. The method of claim 1, wherein the toothpaste has a neutral pH value.

7. The method of claim 1, wherein said toothpaste provides a relative dentin abrasivity ("RDA") value of at least 750.

8. The method of claim 1, further comprising the steps of:
   providing a polishing pad configured to receive the toothpaste; and
   adding a first quantity of the toothpaste to the polishing pad.

9. The method of claim 8, wherein said polishing pad comprises polyurethane.

10. A method for polishing a tooth surface, the method comprising the steps of:
   providing a toothpaste comprising a plurality of inorganic abrasive nanoparticles, the inorganic abrasive particles comprising one or more of silica, ceria, titania, zirconia, silicon nitrite, and silica carbide, wherein said plurality of inorganic abrasive particles comprise an average size of approximately 60 nm, and further wherein the inorganic abrasive particles are sufficiently hard to be abrasive;

adding first quantity of the toothpaste to a polishing pad configured to receive the toothpaste; and polishing a tooth surface with the polishing pad such that a roughness of the tooth surface is reduced, wherein said polishing step results in a tooth surface smoothness of less than 5 nm.

11. The method of claim 10, wherein the tooth surface is polished for approximately 20 seconds to 2 minutes.

12. The method of claim 10, wherein the toothpaste comprises a neutral pH value.

13. The method of claim 10, wherein said toothpaste comprises a relative dentin abrasivity ("RDA") value of at least 750.

14. The method of claim 10, wherein said polishing pad comprises polyurethane.

15. A method for polishing a tooth surface, the method comprising the steps of:

providing a toothpaste comprising a plurality of inorganic abrasive silica nanoparticles having an average size of approximately 60 nm, wherein the inorganic silica nanoparticles are sufficiently hard to be abrasive, and further wherein the toothpaste has a neutral pH and a relative dentin abrasivity ("RDA") value of at least 750;

adding first quantity of the toothpaste to a polishing pad configured to receive the toothpaste; and polishing a tooth surface with the polishing pad such that a roughness of the tooth surface is reduced to a level wherein a bacterial film growing on the polished surface can be removed by rinsing with water, and further wherein said polishing step results in a tooth surface smoothness of less than 5 nm.

16. The method of claim 15, wherein the tooth surface is polished for approximately 20 seconds to 2 minutes.

17. The method of claim 15, wherein said polishing pad comprises polyurethane.

* * * * *